(12) United States Patent
Hiejima et al.

(10) Patent No.: US 6,464,651 B1
(45) Date of Patent: Oct. 15, 2002

(54) GUIDE WIRE

(75) Inventors: Katsuhiro Hiejima; Wataru Taguchi, both of Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/717,266

(22) Filed: Nov. 22, 2000

(30) Foreign Application Priority Data

Nov. 22, 1999 (JP) .......................................... 11-331675

(51) Int. Cl.$^7$ ................................................ A61B 5/00
(52) U.S. Cl. ................................................. 600/585
(58) Field of Search ............................. 600/433, 434, 600/435, 585

(56) References Cited

U.S. PATENT DOCUMENTS

| | | | |
|---|---|---|---|
| 4,682,607 A | 7/1987 | Vaillancourt et al. | 128/772 |
| 5,251,640 A | 10/1993 | Osborne | 128/772 |
| 5,833,631 A | * 11/1998 | Nguyen | 600/585 |

FOREIGN PATENT DOCUMENTS

| | | |
|---|---|---|
| EP | 0 597 341 A1 | 5/1994 |
| EP | 0826 389 A2 | 3/1998 |
| WO | WO 98/42268 | 10/1998 |

OTHER PUBLICATIONS

Patent Abstracts of Japan vol. 016, No. 156 (C–0930), Apr. 16, 1992 (1992–04–16) & JP 04 009162 A (Terumo Corp.), Jan. 13, 1992 (1992–01–13) *abstract*.

* cited by examiner

*Primary Examiner*—Max Hindenburg
(74) *Attorney, Agent, or Firm*—Kubovcik & Kubovcik (57) ABSTRACT

A guide wire having a flexible distal end portion, uniform outer diameter and no stepped difference in the external surface is provided. The guide wire comprises a core wire 1 having a core body portion 11 having a relatively large cross sectional area of wire and a distal end portion 12 provided at a distal end 111 of the core body portion 11 and having a relatively small cross sectional area of wire, and a resin layer 2 coated on the core wire 1. At least the distal end portion 12 comprises a sparse bundle of a plurality of slender wire filaments 121, and substantially no stepped difference is present between the distal end portion 12 and the core body portion 11. The core body portion 11 is a slender wire filament having a section formed in a circular shape or a bundle of slender wire filaments whose number is more than that of the distal end portion and when used for inserting a catheter for PTCA, the diameter (average) of the core body portion 11 is generally about 0.05 mm to 0.10 mm.

3 Claims, 11 Drawing Sheets

Fig. 3 FABRICATION OF A FLEXIBLE PORTION BY WELDING CORE LINES

Fig. 4  RESIN COAT BY EXTRUSION

Fig. 5 FIXED LENGTH CUTTING

Fig. 6

Fig.7 COMBINATION OF A PLURALITY OF CORE LINES BY WELDING CORE LINES

Fig. 8

Fig. 9  RESIN COAT BY EXTRUSION

Fig.10
FIXED LENGTH CUTTING

Fig.11 ROUNDING OF FRONT ENDS AND BASE ENDS

ROUNDING OF FRONT ENDS

ROUNDING OF BASE ENDS

GUIDE WIRE

FIELD OF THE INVENTION

The present invention relates to a guide wire having a flexible distal end for introducing a catheter to a desired part in a blood vessel of a human body for treatment or examination, such as angiography, a blood vessel occlusion technique, a vasodilation technique or the like.

BACKGROUND OF THE INVENTION

A guide wire is used to introduce a catheter into a lesion site at which a conventional surgical operation is difficult to carry out, for example, percutaneous transluminal coronary angioplasty (PTCA), cardiovascular angiography, a blood vessel closing operation or the like.

Blood vessels have complicated curvatures and a guide wire is introduced to a desired part through the curved blood vessels. Therefore, a pertinent flexibility is required for a distal end of a guide wire in order to prevent damage to the blood vessels with which the introduced guide wire is brought into contact.

A guide wire usually comprises a core wire made of stainless steel or the like. Conventionally, there is frequently used as a guide wire, a so-called resin coated guide wire in which a distal section of the core wire is coated with a synthetic resin such as tetrafluoroethylene to provide smoothness to a surface of the core. In this resin coated guide wire, the distal section of the core wire is tapered to thereby provide flexibility in order to facilitate in selecting a blood vessel in which the wire is to be inserted or in reaching a desired part and preventing damage to the blood vessel.

Such tapering processing can be carried out by subjecting a straight core wire to a grinder referred to as a centerless grinder or by dipping a portion of a core wire to be a distal section in an electrolyte solution and pulling up the portion successively and slowly from the solution.

The core wire can be coated with a resin by a resin extruder. However, one tapered short core wire must be separately coated with a resin. Accordingly, a distal end of the tapered short core wire is conventionally welded to a proximal end of another tapered short core wire by a laser or an arc welder to become a certain length of wire. Thereafter, the connected wire is coated with a resin continuously and cut at the thinnest parts of the connected wire into relatively short pieces that become a core wire having both distal and proximal ends. Then there is carried out a so called rounding process in which the cut and exposed cross section of both the distal end and proximal end of the core wire are coated with a resin.

However, according to such a conventional process, joint portions of the core wire become extremely slender and when a resin is extruded onto the surface of the core wire under a constant extruding pressure, the pressure is temporarily reduced at the joint portion and an amount of extruded resin varies according to the diameter of the core wire. Therefore, there are posed problems in which a stepped outer surface is produced on the joint portions, or the joint portions become more slender than unfabricated portions, flexibility differs with each guide wire and an influence is effected on an outer diameter of a straight portion on a proximal end of the core wire.

SUMMARY OF THE INVENTION

The present invention has been carried out in view of the above-described situation and it is an object thereof to provide a guide wire having a flexible distal end portion, and an uniform outer diameter along the entire length of the core without a stepped surface.

The present inventors, as a result of an intensive study in order to resolve the above-described problems, have conceived that a front end portion of a core wire can be constituted by a plurality of slender wire filaments and a cross sectional area of the front end portion of the core wire can be made smaller than a sectional area of a base end portion thereof, and flexibility can be provided to the front end portion of the core wire and completed the present invention. The cross sectional area of the front end portion of the core wire referred to herein means the area occupied by the wire filaments.

That is, the present invention relates to a guide wire having a flexible distal end and comprising a core wire 1 which comprises a core body portion 11 relatively larger in terms of cross sectional area of wire and a distal end portion 12 which is relatively smaller in terms of cross sectional area of wire provided on the distal end of the core body portion 11, and a resin envelope 2 covering the core wire 1, wherein at least said distal end portion 12 comprises a sparse bundle of a plurality of slender wire filaments, and the core wire 1 has substantially no stepped difference between the core body portion 11 and the distal end portion 12.

In the present invention, the core wire 1 comprises a core body portion 11 and a distal end portion 12, and may be constructed such that the distal end portion 12 thereof is provided at an end face of the distal end side of the core body portion 11 such that an outer periphery of the core body portion 11 coincides with an outer periphery of the distal end portion 12. Alternatively, the core wire 1 maybe constructed such that the core wire 1 comprises a plurality of relatively long slender wire filaments in an outer portion of the core wire 1 and a plurality of relatively short slender wire filaments in an inner portion of the core wire 1, and the proximal ends of the wire filaments of the core wire 1 are bundled and fixed to coincide with each other. Incidentally, the sparse bundle of the slender wire filaments refers to an assembly of a plurality of slender wire filaments having clearances among contiguous ones of the slender wire filaments.

An explanation is given of embodiments according to the present invention with reference to the drawings as follows.

Figure 1:
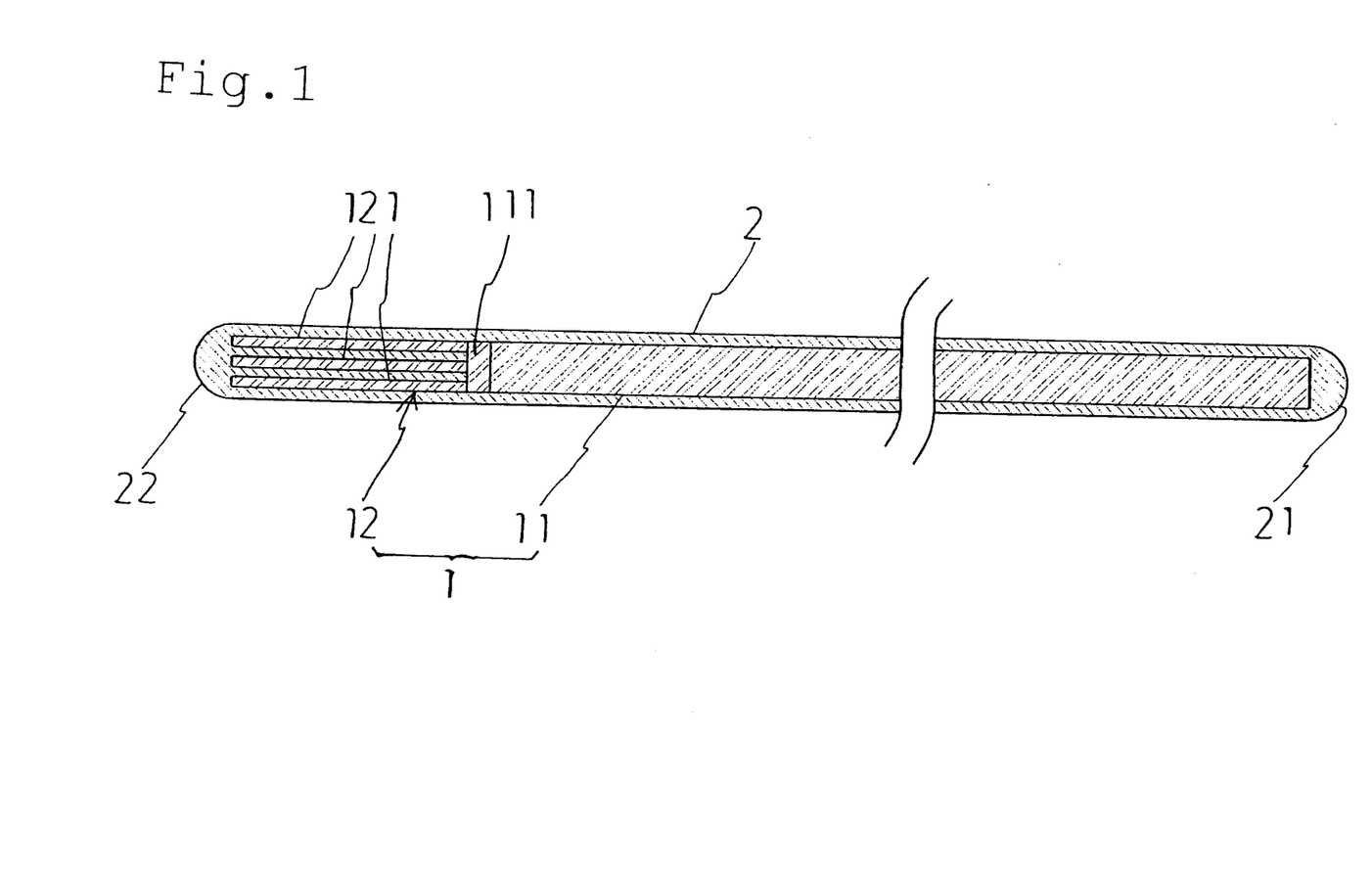
FIG. 1 is a longitudinal sectional view showing an embodiment of the invention.
Figure 2:
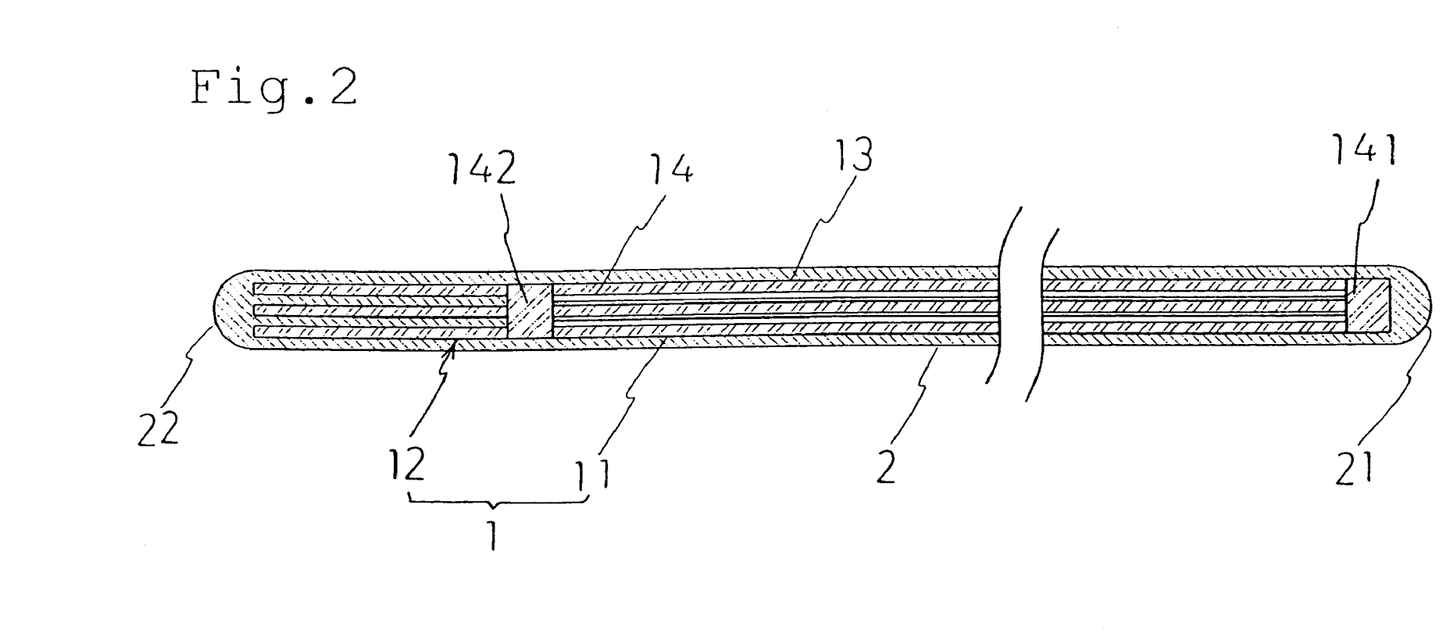
FIG. 2 is a longitudinal sectional view showing another embodiment of the invention.

FIG. 1 is a longitudinal sectional view showing an embodiment of the present invention and FIG. 2 is a longitudinal sectional view showing another embodiment of the present invention. Further, FIG. 3 to FIG. 6 are explanatory views of fabrication steps of a guide wire as shown in FIG. 1, and FIG. 7 to FIG. 11 are explanatory views of fabrication steps of a guide wire as shown in FIG. 2.

As shown in FIG. 1 and FIG. 2, a guide wire according to the present invention includes a core wire 1 having a core body portion 11 having a relatively large cross sectional area of wire and a distal end portion 12 provided at a distal end 111 of the core body portion 11 and having a relatively small cross sectional area of wire, at least the distal end portion 12 comprising a sparse bundle of a plurality of slender wire filaments 121 and having substantially no stepped difference (surface) between the distal end portion 12 and the core body portion 11, and a resin layer 2 coated on the core wire 1.

According to the guide wire illustrated in FIG. 1, the core wire 1 comprises core body portion 11 and distal end portion 12 provided at distal end 111 of the core body portion 11. Distal end portion 12 comprises a sparse bundle of a plurality of slender wire filaments 121 provided at an end face of the distal end 111 of the core body portion 11 such that an outer periphery of the distal end portion 12 coincides with an outer periphery of the end face. The core body portion 11 is a slender wire filament, a cross section of which is formed in a circular shape. When the guide wire is used for inserting a catheter for PTCA, a diameter (average) of the core body portion 11 is generally about 0.05 mm to 0.10 mm. Although the distal end portion 12 may be constructed such that the plurality of slender wire filaments 121 is previously formed adjacent to the distal end side of the core body portion 11, the distal end portion 12 may be constructed such that the plurality of slender wire filaments 121 is connected with the distal end 111 of the core body portion 11 by welding or the like. Although the diameter of each of the slender wire filaments 121 may be less than half of the diameter of the core body portion 11, a diameter of about a quarter to one eighth thereof is preferable.

A guide wire shown by FIG. 2 comprises a core wire 1 which comprises a plurality of relatively long slender wire filaments 13 existing in an outer portion of the core wire 1 and in both the core body portion 11 and distal end portion 12 and a plurality of relatively short slender wire filaments 14 existing in an inner portion of the core wire 1 and in core body portion 11. The number of the slender wire filaments in the distal end portion 12 is less than that of the core body portion 11. The slender wire filaments 13 and 14 of the core body portion 11 are bundled and fixed such that base end sides thereof coincide with each other. In this case, the front end portion of the relatively long slender wire filaments 13, that is, portions thereof projected to the outside of, or beyond, the relatively short slender wire filaments 14 constitute the flexible distal end portion 12 after being coated with a resin. Although diameters of the slender wire filaments 13 and 14 may be less than half of the diameter of the core wire 1, about a quarter to one eighth is preferable. The slender wire filaments 13 and 14 can be fixed by welding at least portions of the slender wire filaments 14 including base ends 141 and distal ends 142 at certain intervals by spot welding (see, FIG. 8).

Figure 10:
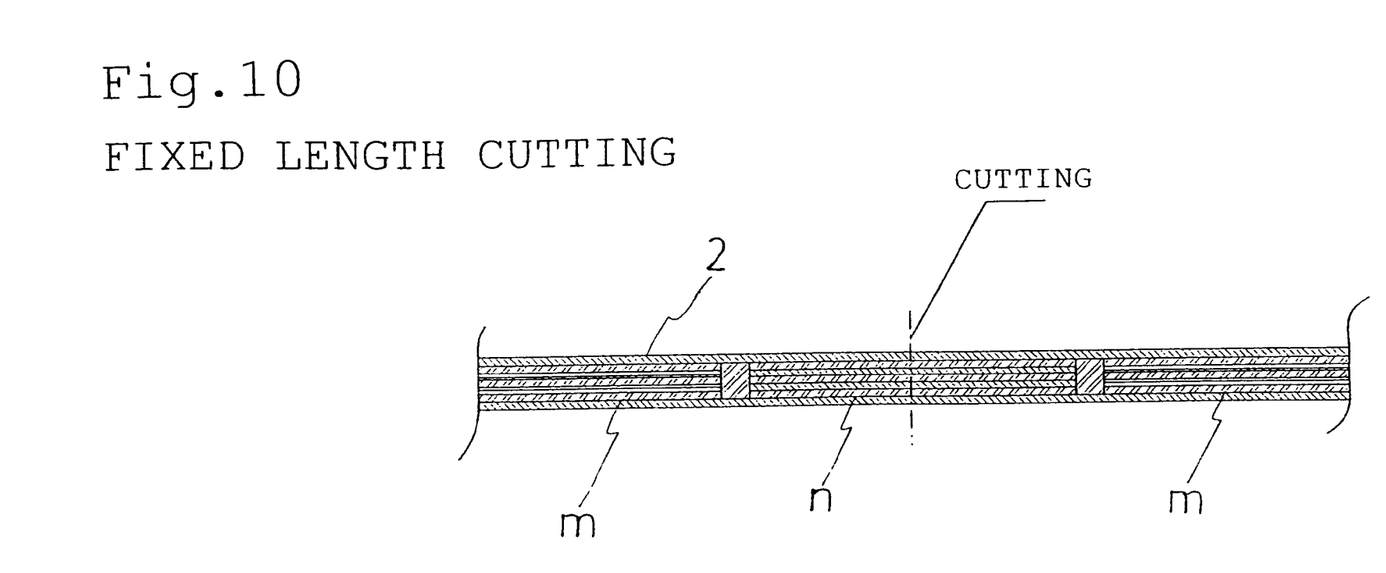
Figure 11:
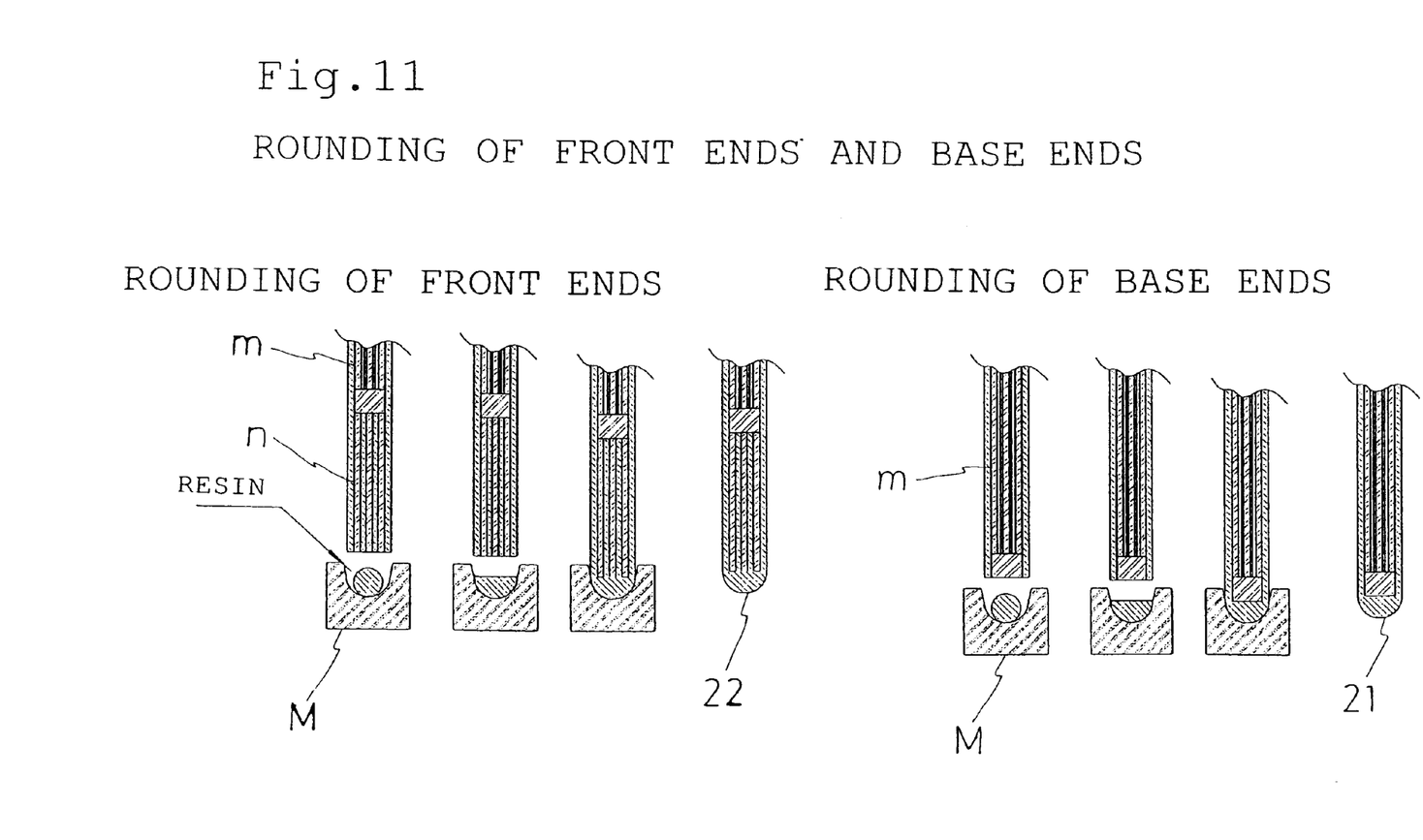

Further, in fabricating the guide wire of this type, it is efficient to weld the slender wire filaments at certain intervals by spot welding (see, FIG. 7), reduce a number of the slender wire filaments, for instance, by a cutter in a certain zone (see, FIGS. 7 and 8, "n" part), coat the surface of the core wire 1 with a resin (see, FIG. 9), cut the reduced part separately (see, FIG. 10, "n" part) and round the distal end to thereby form the distal end portion 12 (see FIG. 11).

As a material of the core wire 1, there can be adopted a super-elastic alloy or a high rigid alloy to meet pertinent flexibility, torque transmitting performance, kink resistance or the like required of a guide wire. Super-elastic alloys include nickel series alloys, i.e., nickel-titanium alloys, nickel-titanium-cobalt alloys, nickel-titanium-iron alloys, nickel-aluminum-alloys, nickel-titanium-cobalt alloys; copper series alloys, i.e., copper-aluminum-nickel alloys, copper-zinc alloys, copper-zinc-X alloys (where X is beryllium, silicon, aluminum, or cobalt); titanium series of titanium-palladium-X alloys (where X is chromium, manganese, nickel, iron, cobalt, tungsten, or tantalum); iron series alloys, i.e., iron-manganese alloys and the like. High rigidity alloys include stainless steel, cobalt-nickel-chromium-molybdenum-niobium alloys, nickel-iron-chromium-molybdenum alloys and the like.

As a coating material of the core wire 1, there can be adopted polyurethane, polyamide, fluoroplastics including polytetrafluoroethylene, ethylene-tetrafluoroethylene copolymer or the like, polyvinyl chloride, ethylene-vinyl acetate copolymer, silicone, polybutadiene, polyethylene, thermoplastic elastomer and the like. The thickness of the coating layer depends on intended use, but generally, is 0.05 mm to 0.5 mm.

The diameter of the core wire 1 may be commonly 0.03 mm to 1.0 mm and, preferably, 0.05 to 0.10 mm for PTCA, and 0.3 mm to 0.8 mm for angiography. The length of the distal end portion 12, the core body portion 11 and the core wire 1 may be selected in accordance with intended use. Usually, the length of the distal end portion 12 is less than that of the core body portion 11.

Additionally, an explanation is given of methods of fabricating a guide wire according to the present invention with reference to the drawings.

EMBODIMENT 1

An explanation is given below of a method of fabricating the guide wire shown in FIG. 1 with reference to FIG. 3 to FIG. 6.

Figure 3:
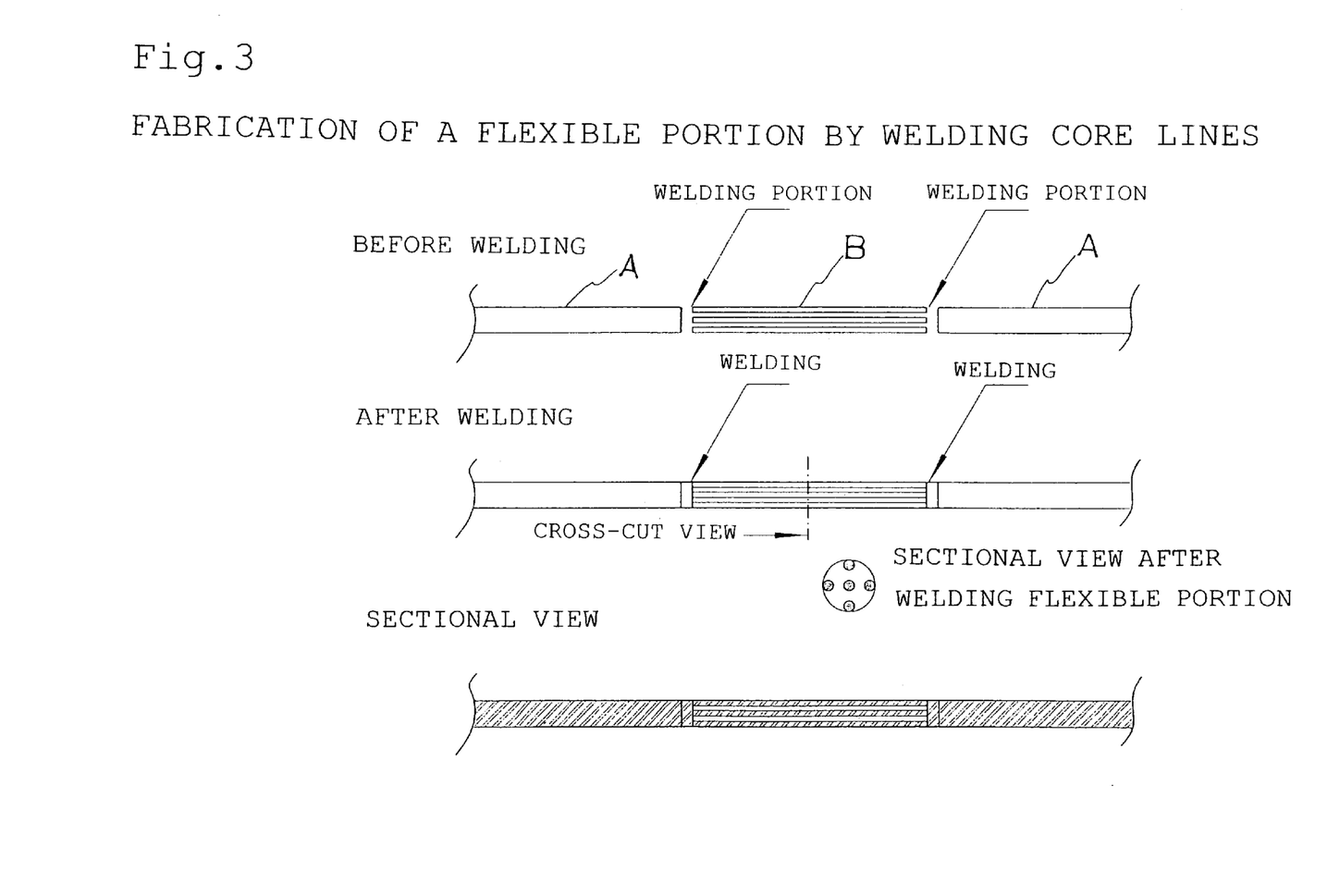
FIGS. 3 to 6 are explanatory views of steps of fabricating the guide wire shown in FIG. 1.
Figure 4:
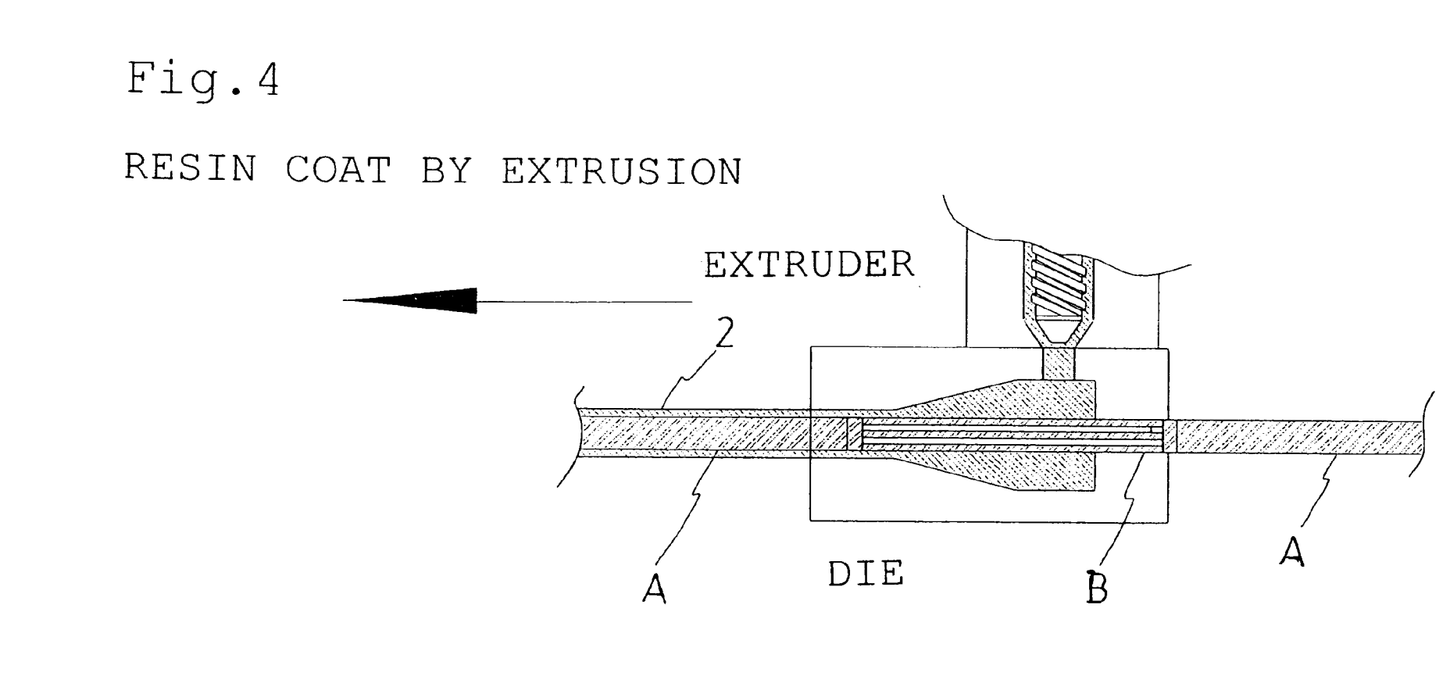
Figure 5:
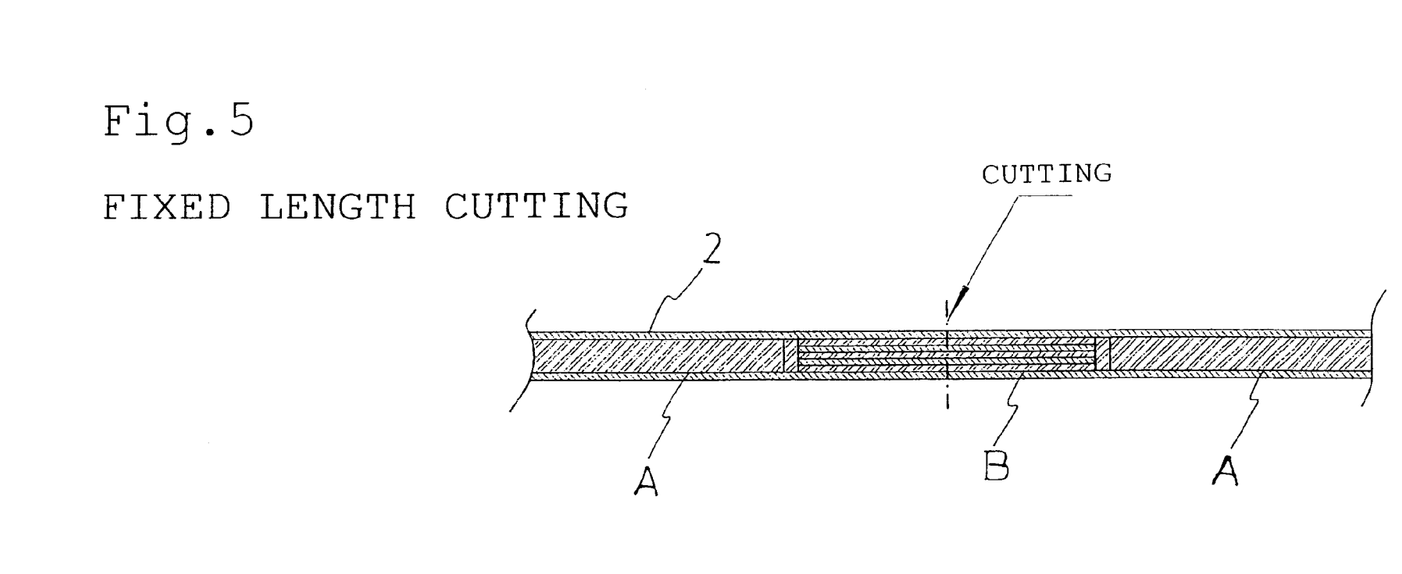
Figure 6:
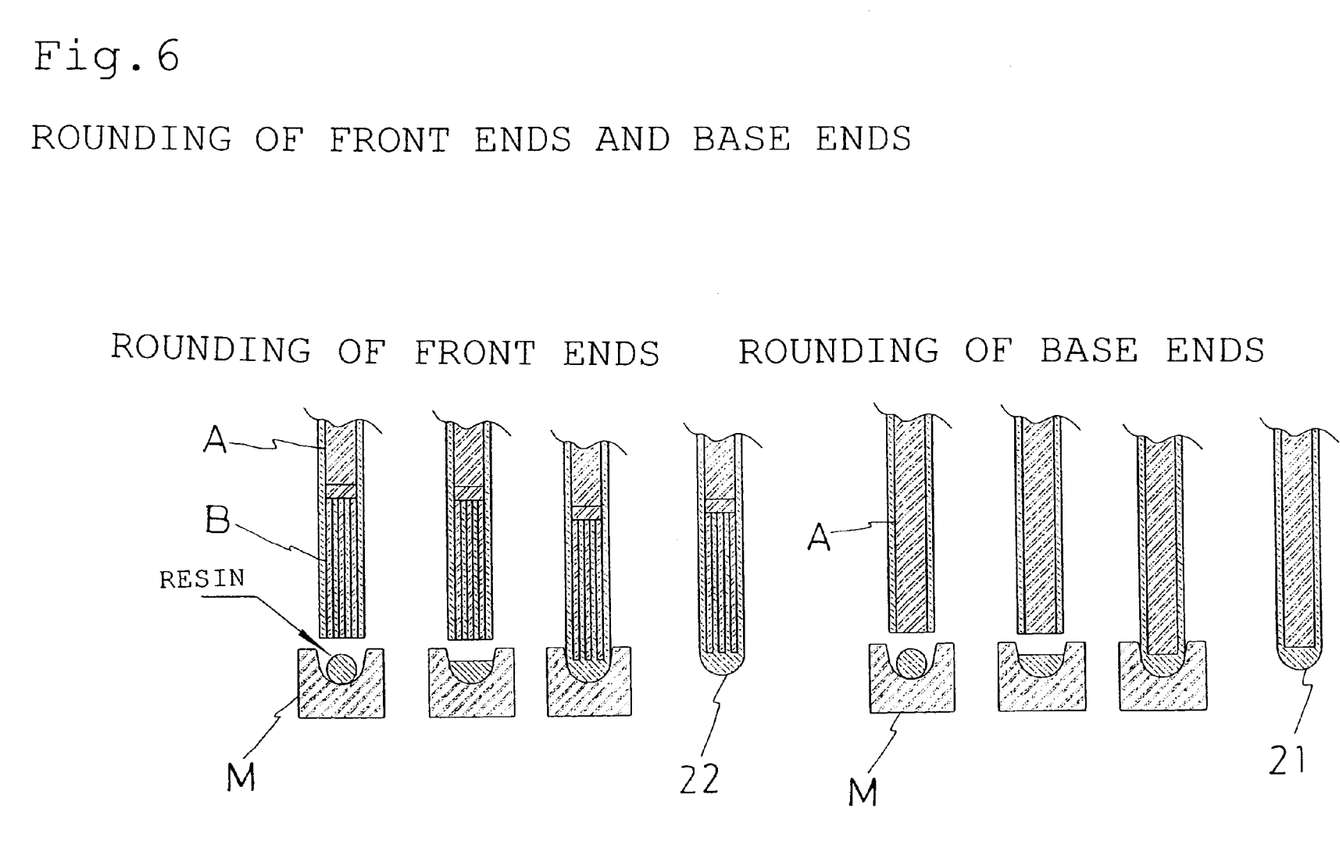

First, as illustrated in FIG. 3, a relatively thick slender wire filament A having a diameter of 0.45 mm constituting the core body portion 11 and a sparse bundle B of a plurality of relatively slender wire filaments (five pieces) constituting the distal end portion 12, are fixedly welded to each other such that an outer periphery of B and an outer periphery of A coincide with each other to thereby form a wire filament member in which A and B are aligned alternately in the order A, B, A, B. Next, the wire filament member is subjected to a resin extruder, coated with resin (see, FIG. 4) and cut at a center part of A (not shown) and B as illustrated in FIG. 5. Finally, as illustrated in FIG. 6, the cut wire filament member coated with a resin, is subjected to a die M to round the ends of the wire filament member, to thereby form a distal end 22 (see, FIG. 6, left) and a base end 21 (see, FIG. 6, right) of the guide wire. In FIG. 6, left, the resin is positioned and melted in a cavity of the die M, and the cut wire filament member of the sparse bundle B is inserted in the cavity and pulled out from the die M to form the rounded distal end 22 of the distal end portion 12. In FIG. 6, right, the resin is also positioned and melted in a cavity of the die M, and the cut wire filament member of the thick slender wire filament is inserted in the cavity and pulled out from the die M to form the rounded base end 21 of the core body portion 11.

An explanation will now be given of a method of fabricating the guide wire shown in FIG. 2 with reference to FIG. 7 to FIG. 11.

Figure 7:
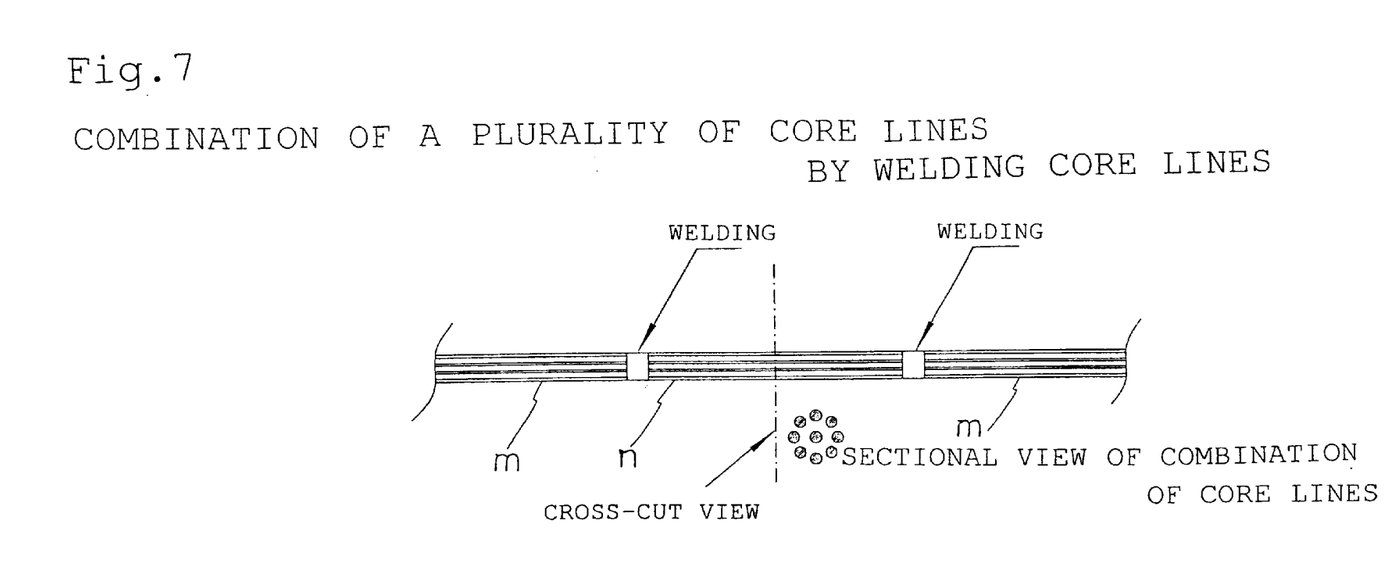
FIGS. 7 to 11 are explanatory views of steps of fabricating the guide wire shown in FIG. 2.

First, a bundle of long slender wire filaments (nine pieces in FIG. 7) is prepared, and as illustrated in FIG. 7, an appropriate part of the bundle is welded to form a relatively long portion "m" including a weld portion and a relatively short portion "n" not including a weld portion so as to produce repeating segments m-n-m, and to thereby fabricate a wire filament member. Next, a plurality of pieces (five pieces in FIG. 8) of slender wire rods (nine pieces in FIG.

Figure 8:
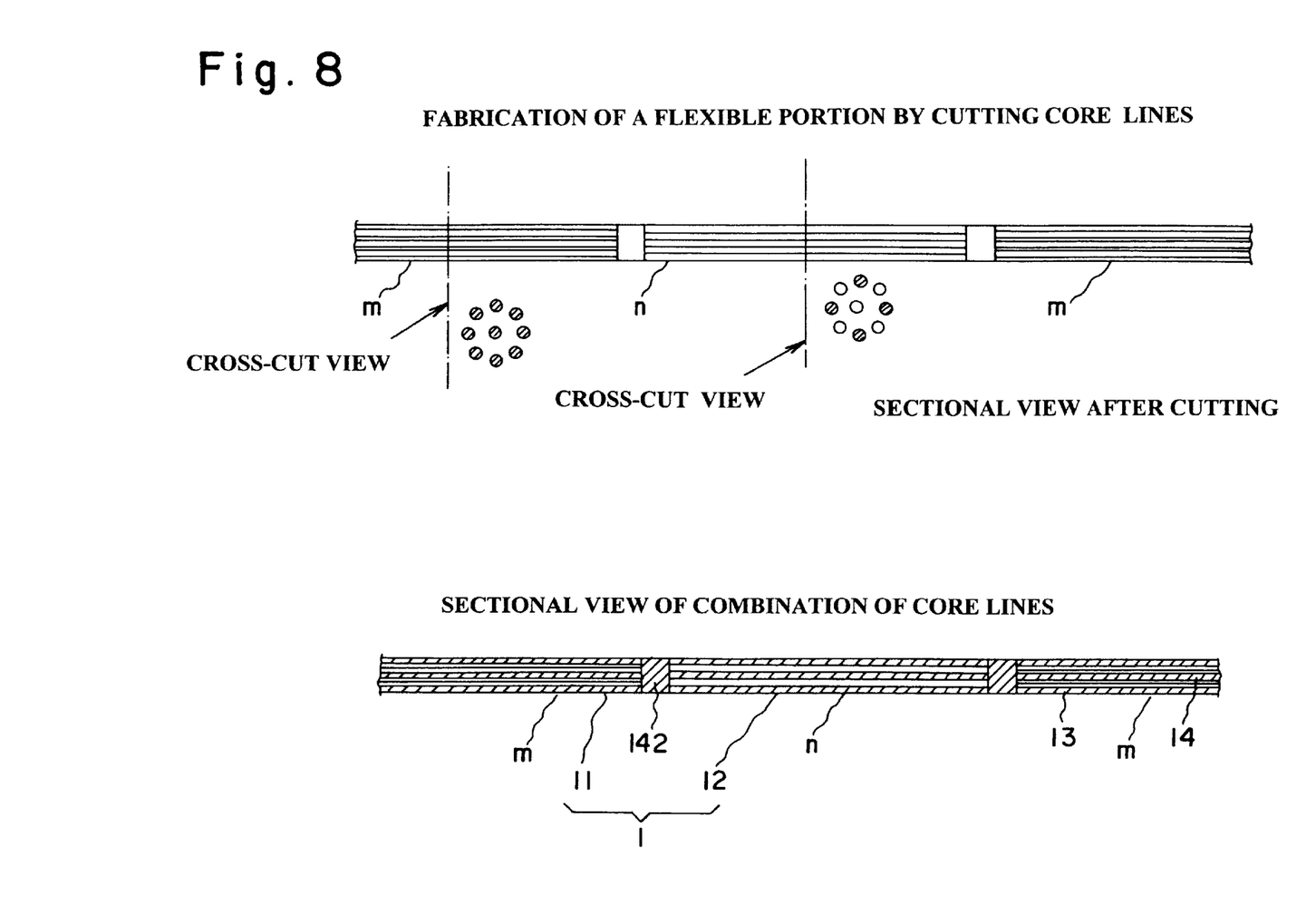
Figure 9:
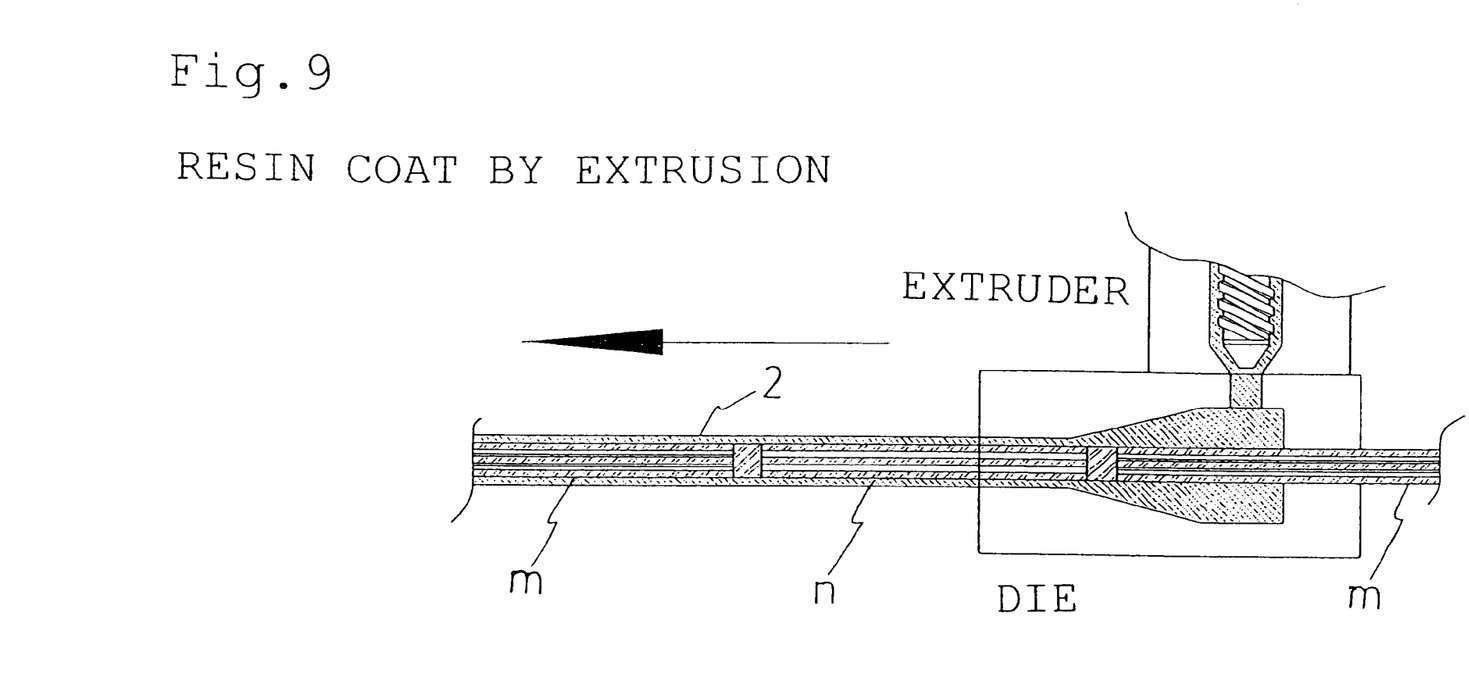

8) at the relatively short portions "n" are cut axisymmetrically to thereby form portions corresponding to flexible distal end portions. In FIGS. 7 and 8, black circles mean the wire filaments, and in FIG. 8, white circles mean the reduced (cut) wire filaments. Then, the wire filament member is subjected to a resin extruder and coated with a resin (see, FIG. 9) and thereafter, as illustrated in FIG. 10, cutting is carried out at centers of the weld portions where the relatively long portions "m" are contiguous to each other as well as in the center of the relatively short portions "n". Finally, as illustrated in FIG. 11, the cut wire filament member coated with the resin is treated in the die M to thereby round the wire filament member and to thereby form the rounded distal end 22 and the rounded base end 21 of the guide wire.

As is apparent from the above-explanations, according to the present invention, the flexible distal end portion 12 of a guide wire is constructed of a sparse bundle of a plurality of relatively slender wire filaments provided such that the outer periphery of the bundle coincides with the outer periphery of the core body portion 11. Accordingly, there can be formed a guide wire having a flexible distal end portion 12 and having a uniform outer diameter with no stepped difference between the core body portion 11 and the distal end portion 12. Further, by changing the thickness (diameter) of the relatively slender wire filaments or arranging the slender wire filaments sparsely and densely, a directionality can be provided to running of the guide wire.

What is claimed is:

1. A guide wire having a flexible distal end and comprising a core wire 1 which comprises a core body portion 11 relatively larger in cross sectional area and a distal end portion 12 relatively smaller in cross sectional area provided on a distal end of the core body portion 11, and a resin envelope 2 covering the core wire 1, wherein said distal end portion 12 consists essentially of a sparse bundle of a plurality of slender wire filaments; the core wire 1 having an uniform outer diameter along its length and substantially no stepped difference between the core body portion 11 and the distal end portion 12.

2. A guide wire according to claim 1, wherein the distal end portion 12 of the core wire 1 is provided on a front end of the core body portion 11 such that an outer periphery of the distal end portion 12 coincides with an outer periphery of the front end of the core body portion 11.

3. A guide wire according to claim 1, wherein the core wire 1 comprises a plurality of a relatively long slender wire filaments in an outer side of the core wire 1 and a plurality of relatively short slender wire filaments in an inner side of the core wire 1, and the proximal ends of the relatively long wire filaments and the relatively short wire filaments are bundled and fixed to coincide with each other.

* * * * *